United States Patent
Aftab et al.

(10) Patent No.: US 11,065,240 B2
(45) Date of Patent: Jul. 20, 2021

(54) DRUG COMBINATIONS TO TREAT MULTIPLE MYELOMA

(71) Applicant: Exelixis, Inc., South San Francisco, CA (US)

(72) Inventors: Dana T. Aftab, San Rafael, CA (US); Peter Lamb, Oakland, CA (US)

(73) Assignee: Exelixis, Inc., Alameda, CA (US)

( * ) Notice: Subject to any disclaimer, the term of this patent is extended or adjusted under 35 U.S.C. 154(b) by 0 days.

(21) Appl. No.: 15/501,582

(22) PCT Filed: Aug. 5, 2015

(86) PCT No.: PCT/US2015/043825
§ 371 (c)(1),
(2) Date: Feb. 3, 2017

(87) PCT Pub. No.: WO2016/022697
PCT Pub. Date: Feb. 11, 2016

(65) Prior Publication Data
US 2017/0224672 A1    Aug. 10, 2017

Related U.S. Application Data

(60) Provisional application No. 62/033,386, filed on Aug. 5, 2014.

(51) Int. Cl.
| A61K 31/47 | (2006.01) |
| A61K 38/05 | (2006.01) |
| A61K 31/194 | (2006.01) |
| A61K 31/69 | (2006.01) |
| A61K 31/4965 | (2006.01) |

(52) U.S. Cl.
CPC ............ *A61K 31/47* (2013.01); *A61K 31/194* (2013.01); *A61K 31/4965* (2013.01); *A61K 31/69* (2013.01); *A61K 38/05* (2013.01)

(58) Field of Classification Search
CPC .................................................... A61K 31/47
See application file for complete search history.

(56) References Cited

U.S. PATENT DOCUMENTS

| 7,579,473 | B2 * | 8/2009 | Bannen .................. A61K 31/47 546/153 |
| 7,977,345 | B2 | 7/2011 | Bannen et al. |
| 7,999,006 | B2 | 8/2011 | Lamb |
| 8,067,436 | B2 | 11/2011 | Bannen et al. |
| 8,178,532 | B2 | 5/2012 | Bannen et al. |
| 8,314,232 | B2 | 11/2012 | Deschamps et al. |
| 8,476,298 | B2 | 7/2013 | Bannen et al. |
| 8,497,284 | B2 | 7/2013 | Bannen et al. |
| 8,673,912 | B2 | 3/2014 | Cannon et al. |
| 8,877,776 | B2 | 11/2014 | Brown et al. |
| 9,174,947 | B2 | 11/2015 | Bannen et al. |
| 9,365,516 | B2 | 6/2016 | Wilson et al. |
| 9,717,720 | B2 | 8/2017 | Wilson et al. |
| 9,724,342 | B2 | 8/2017 | Wilson et al. |
| 9,809,549 | B2 | 11/2017 | Brown et al. |
| 9,861,624 | B2 | 1/2018 | Aftab et al. |
| 9,969,692 | B2 | 5/2018 | Wilson et al. |
| 10,034,873 | B2 | 7/2018 | Wilson et al. |
| 10,039,757 | B2 | 9/2018 | Wilson et al. |
| 10,159,666 | B2 | 12/2018 | Aftab et al. |
| 10,166,225 | B2 | 1/2019 | Aftab et al. |
| 10,273,211 | B2 | 4/2019 | Aftab et al. |
| 2008/0161305 | A1 | 7/2008 | Forsyth et al. |
| 2009/0274693 | A1 | 11/2009 | Gilmer et al. |
| 2011/0077233 | A1 | 3/2011 | Bannen et al. |
| 2012/0070368 | A1 | 3/2012 | Bannen et al. |
| 2012/0184523 | A1 | 7/2012 | Bannen et al. |
| 2012/0252840 | A1 | 10/2012 | Aftab et al. |
| 2012/0282179 | A1 | 11/2012 | Aftab et al. |
| 2013/0030172 | A1 | 1/2013 | Wilson et al. |
| 2013/0142790 | A1 | 6/2013 | Gilmer et al. |
| 2013/0143881 | A1 | 6/2013 | Cannon et al. |
| 2013/0150363 | A1 | 6/2013 | Gilmer et al. |
| 2013/0197230 | A1 | 8/2013 | Wilson et al. |
| 2013/0252940 | A1 | 9/2013 | Bannen et al. |
| 2013/0252956 | A1 | 9/2013 | Kallender et al. |
| 2013/0330377 | A1 | 12/2013 | Wilson |
| 2014/0057908 | A1 | 2/2014 | Smith et al. |
| 2014/0057943 | A1 | 2/2014 | Smith et al. |
| 2014/0066444 | A1 | 3/2014 | Smith et al. |
| 2014/0121239 | A1 | 5/2014 | Aftab |
| 2014/0155396 | A1 | 6/2014 | Bannen et al. |
| 2014/0179736 | A1 | 6/2014 | Schwab et al. |
| 2014/0221372 | A1 | 8/2014 | Kulkarni et al. |
| 2014/0228401 | A1 | 8/2014 | Aftab et al. |
| 2014/0256938 | A1 | 9/2014 | Wilson et al. |
| 2014/0302012 | A1 | 10/2014 | Aftab et al. |

(Continued)

FOREIGN PATENT DOCUMENTS

| WO | 2013119693 | * | 8/2013 |
| WO | 2013119693 | A1 | 8/2013 |

OTHER PUBLICATIONS

Roodman, Expert Opin, Ther. Targets, vol. 12(11), 2008, 1377-1387. (Year: 2008).*
Canadas, Israel, et al., "C-MET as a new therapeutic target for the development of novel anticancer drugs", Clinical & Translational Oncology, col. 12, No. 4, Apr. 2010.
Milligan, Shawn A., et al., "The green tea polyphenol EGCG potentiates the antiproliferative activity of c-Met and epidermal growth factor receptor inhibitors in non-small cell lung cancer cells", Clinical Cancer Research, col. 15, No. 15, Aug. 1, 2009.
Moschetta, Michele, et al., "Novel targeting of phospho-cMET overcomes drug resistance and induces antitumor activity in multiple myeloma", Clinical Cancer Research, vol. 19, No. 16, Aug. 15, 2013.

(Continued)

*Primary Examiner* — D Margaret M Seaman
(74) *Attorney, Agent, or Firm* — Honigman LLP; Heidi M. Berven

(57) ABSTRACT

This invention relates to the combination of a C-Met inhibitor and a proteasome inhibitor to treat cancer, particularly multiple myeloma.

4 Claims, 1 Drawing Sheet

(56) References Cited

U.S. PATENT DOCUMENTS

| | | |
|---|---|---|
| 2014/0323522 A1 | 10/2014 | Aftab et al. |
| 2015/0057310 A1 | 2/2015 | Brown et al. |
| 2015/0133494 A1 | 5/2015 | Aftab et al. |
| 2015/0196545 A1 | 7/2015 | Aftab et al. |
| 2015/0202196 A1 | 7/2015 | Bannen et al. |
| 2015/0238477 A1 | 8/2015 | Aftab |
| 2015/0376133 A1 | 12/2015 | Bannen et al. |
| 2016/0000772 A1 | 1/2016 | Aftab et al. |
| 2016/0022662 A1 | 1/2016 | Decillis et al. |
| 2016/0031818 A1 | 2/2016 | Aftab et al. |
| 2016/0051532 A1 | 2/2016 | Aftab et al. |
| 2016/0082019 A1 | 3/2016 | Sweeney et al. |
| 2016/0185725 A1 | 6/2016 | Bannen et al. |
| 2016/0220554 A1 | 8/2016 | Smith et al. |
| 2016/0229805 A1 | 8/2016 | Wilson et al. |
| 2017/0042880 A1 | 2/2017 | Aftab et al. |
| 2017/0044106 A1 | 2/2017 | Aftab et al. |
| 2017/0057921 A1 | 3/2017 | Wilson et al. |
| 2017/0143689 A1 | 5/2017 | Wilson et al. |
| 2017/0217896 A1 | 8/2017 | Donnelly et al. |
| 2017/0224670 A1 | 8/2017 | Smalley |
| 2017/0224672 A1 | 8/2017 | Aftab et al. |
| 2017/0266178 A1 | 9/2017 | Wilson et al. |
| 2017/0275251 A1 | 9/2017 | Brown et al. |
| 2017/0355678 A1 | 12/2017 | Bannen et al. |
| 2018/0002289 A1 | 1/2018 | Brown et al. |
| 2018/0037552 A1 | 2/2018 | Brown et al. |
| 2018/0230100 A1 | 8/2018 | Wilson et al. |
| 2018/0311229 A1 | 11/2018 | Wilson et al. |
| 2019/0030021 A1 | 1/2019 | Wilson et al. |
| 2019/0076420 A1 | 3/2019 | Aftab et al. |
| 2019/0091215 A1 | 3/2019 | Aftab et al. |
| 2019/0151302 A1 | 5/2019 | Aftab et al. |

OTHER PUBLICATIONS

Kubiczkova, et al., "Proteasome inhibitors—molecular basis and current perspecitves in multiple myeloma", Journal of Cellular and Molecular Medicine, vol. 18, No. 6, pp. 947-961, Jun. 2014.

Que, Wenzhong, et al., "Knockdown of c-Met enhances sensitivity to bortezomib in human multiple myeloma U266 cells via inhibiting Akt/mTOR activity", APMIS, vol. 120, No. 3, pp. 195-203, Oct. 25, 2011.

Vaishampayan, Ulka, "Cabozantinib as a Novel Therapy for Renal Cell Carcinoma", Curr. Oncol. Rep., vol. 15, pp. 76-82, Jan. 5, 2013 (Jan. 5, 2013).

Yakes, et al., "Cabozantinib (XL184), a novel MET and VEGFR2 inhibitor, simultaneously suppresses metastasis, angiogenesis and tumor growth", Mol Cancer Ther, No. 10, pp. 2298-2308, Sep. 16, 2011.

Yang, et al., "Clinical development of novel proteasome inhibitors for cancer treatment", Expert Opinions in Investigational Drugs, vol. 18, No. 7, pp. 957-971, Jul. 2009.

Yoneda, Toshiyuki, "Role of marrow stromal cells in the progression of bone destruction in multiple myeloma", Journal of Clinical end Experimental Medicine, 2012, vol. 242, No. 13, pp. 1002-1008.

Suominen, et al. Poster 734: Effects of Cabozantinib in the 5TGM1 Murine Multiple Myeloma Model.

International Search Report for PCT/US2015/043825, dated Oct. 16, 2015.

Roodman, G. David, "Novel targets for myeloma bone disease," Expert Opinion on Therapeutic Targets, vol. 12, No. 11, pp. 1377-1387, Oct. 14, 2008.

* cited by examiner

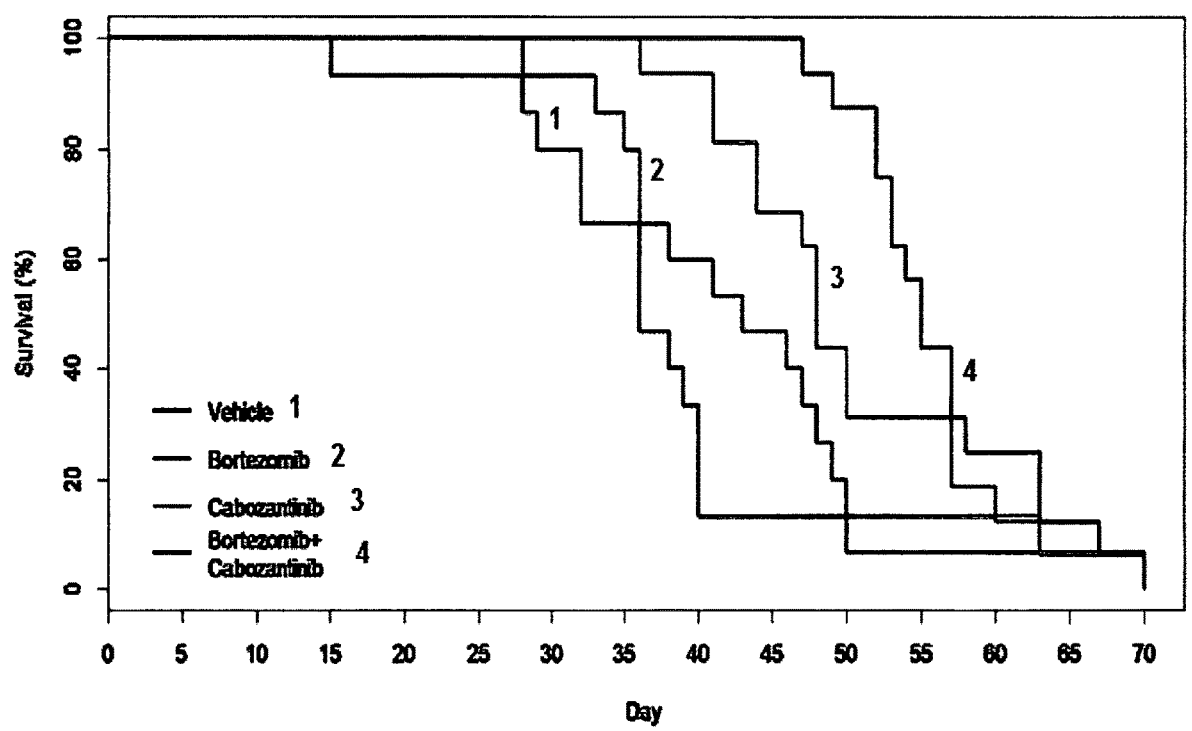

DRUG COMBINATIONS TO TREAT MULTIPLE MYELOMA

CROSS-REFERENCE TO RELATED APPLICATIONS

This application is a United States National Phase filing of PCT/US2015/043825, filed Aug. 5, 2015, which claims the benefit of U.S. Provisional Application No. 62/033,386, filed Aug. 5, 2014, the entire contents of which are incorporated herein by reference.

FIELD OF INVENTION

This invention relates to the combination of cabozantinib and a proteasome inhibitor to treat cancer, particularly multiple myeloma.

BACKGROUND OF THE INVENTION

Significant improvements in overall survival and remission duration in patients with multiple myeloma (MM) are attributable in large measure to the development of new therapeutic agents such as proteasome inhibitors (PIs). Proteasomes serve an important cellular function in enabling clearance of abnormal or mutant proteins. Tumor cells are heavily dependent on this clearance mechanism and thus are susceptible to proteasome inhibition. Proteasome inhibition culminates in antiproliferative and pro-apoptotic effects that are mediated via induction of endoplasmic reticulum stress, activation of caspases, and reactive oxygen species.

For many years, bortezomib (Velcade) was the only available agent in the PI class of drugs. Bortezomib is a dipeptide boronate compound that is administered intravenously or subcutaneously. Bortezomib is a reversible inhibitor of the chymotrypsin-like catalytic activity of the β5 subunit of the 20S mammalian proteasome. Approved by the FDA in 2003 for the treatment of refractory multiple myeloma, bortezomib was subsequently expanded for first-line combination use, typically with dexamethasone or as part of a three-drug combination such as Velcade-Revlimid-dexamethasone (VRD) or Velcade-cyclophosphamide-dexamethasone (VCD or CyBorD/Cybord).

Patients being treated with bortezomib have been found to develop peripheral neuropathy and eventual drug resistance as a result of overexpression of the β5 subunit, mutation of active drug binding sites, or downstream upregulation of survival pathways.

As a result, to avoid the shortcomings of existing bortezomib treatments, there is a continuing need for new agents and combinations for the treatment of multiple myeloma.

SUMMARY OF THE INVENTION

It has now been found that certain proteasome inhibitors in combination with C-Met inhibitors, are surprisingly effective in the treatment of certain cancers such as multiple myeloma. The new combinations possess one or more attributes, including improvements in the anticancer profile of the combination as compared to single agent treatment; similar or reduced side effect profile of the combination as compared to single agent treatment; and similar or reduced dosing load for the combination as compared to single agent therapy.

Thus, in one aspect, the present disclosure relates to a pharmaceutical combination comprising a proteasome inhibitor and an inhibitor of C-Met according to the formula:

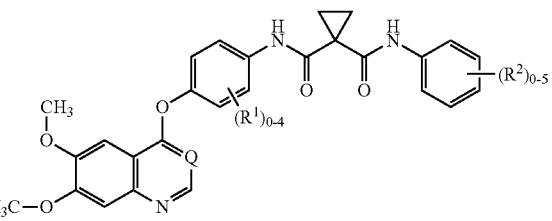

Formula I or a pharmaceutically acceptable salt thereof or a pharmaceutical composition comprising the compound of formula I and a pharmaceutically acceptable carrier, wherein:
$R^1$ is halo;
$R^2$ is halo; and
Q is CH or N.

In one embodiment of this aspect, the C-Met inhibitor is cabozantinib (compound 1, the structure of which is depicted below.

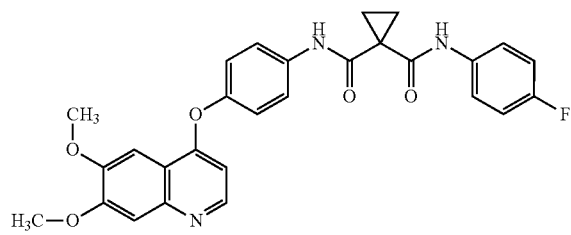

Compound 1

Compound 1 is known by its chemical name N-(4-{[6,7-bis(methyloxy)quinolin-4-yl]oxy}phenyl)-N'-(4-fluorophenyl)cyclopropane-1,1-dicarboxamide and by the name cabozantinib (COMETRIQ™). Cabozantinib is formulated as the L-malate salt of N-(4-{[6,7-bis(methyloxy)quinolin-4-yl]oxy}phenyl)-N'-(4-fluorophenyl)cyclopropane-1,1-dicarboxamide. WO 2005/030140, the entire contents of which is incorporated herein by reference, discloses compound 1 and describes how it is made and also discloses the therapeutic activity of this compound to inhibit, regulate, and/or modulate the signal transduction of kinases (Assays, Table 4, entry 289). In November 2012, cabozantinib achieved regulatory approval in the United States for the treatment of progressive metastatic medullary thyroid cancer. WO 2005/030140 describes the synthesis of cabozantinib (Example 48) and also discloses the therapeutic activity of this molecule to inhibit, regulate, and/or modulate the signal transduction of kinases (Assays, Table 4, entry 289). Example 48 begins at paragraph [0353] in WO 2005/030140. Dosing information for compound 1 is available from the FDA at acessdata.fda-.gov/scripts/cder/drugsatfda/
index.cfm?fuseaction=Search.DrugDetails (last visited Aug. 3, 2014).

In another embodiment of this aspect, the proteasome inhibitor is selected from the group consisting of epigallocatechin-3-gallate, salinosporamide A, carfilzomib, bortezomib, oprozomib, ixazomib, marizomib, or delanzomib.

Also disclosed are methods for using the pharmaceutical combination in the treatment of cancer, particularly multiple myeloma, as well as kits for administration of the pharmaceutical combination. The kit typically includes separate pharmaceutical compositions containing the C-Met inhibitor and the proteasome inhibitor. Alternatively, the kit contains one pharmaceutical composition containing both the C-Met inhibitor and the proteasome inhibitor in the same composition. In any of these embodiments, each pharmaceutical composition may include one or more pharmaceutically acceptable carriers or exipients.

In certain embodiments, the treatments utilize the C-Met inhibitor and the proteasome inhibitor to help to arrest, partially or fully, or to reduce the development of multidrug resistant cancerous cells in a subject. In this embodiment, the combinations may allow a reduced efficacious amount of the proteasome inhibitor to be given to a subject.

SUMMARY OF THE FIGURES

FIG. 1 depicts the median survival times in a murine mouse myeloma model for vehicle, bortezomib, cabozantinib, and cabozantinib+bortezomib.

DETAILED DESCRIPTION

As indicated above, this disclosure relates to pharmaceutical combinations comprising a proteasome inhibitor and a C-Met inhibitor for the treatment of cancer, particularly multiple myeloma.

As used herein, the term "proteasome inhibitor" refers to a class of compounds that act on proteasomes. These compounds prevent degradation of pro-apoptotic factors, permitting activation of programmed cell death in neoplastic cells dependent upon suppression of pro-apoptotic pathways. In normal cells, the proteasome regulates protein expression and function by degradation of ubiquitinylated proteins, and also cleanses the cell of abnormal or misfolded proteins. Proteasome inhibitors include disulfiram (CAS No. 97-77-8), epigallocatechin-3-gallate (CAS No. 989-51-5), salinosporamide A (Marizomib), carfilzomib (CAS No. 868540-17-4), bortezomib (CAS No. 179324-69-7), oprozomib (CAS No. 935888-69-0), ixazomib, and delanzomib, the structure of each of which is depicted below.

Disulfiram

Epigallocatechin-3-gallate

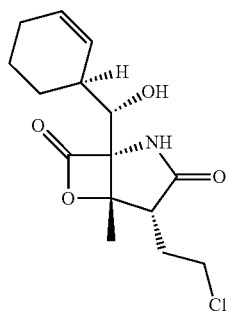

Salinosporamide A

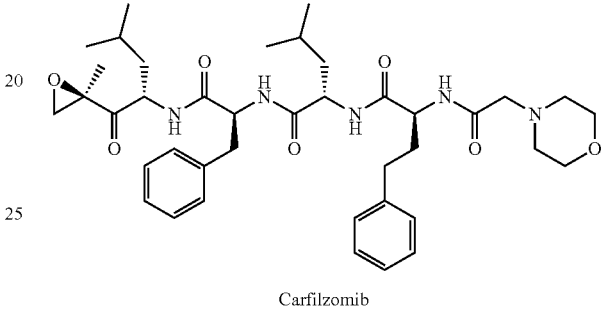

Carfilzomib

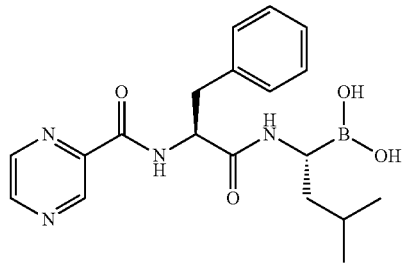

Bortezomib

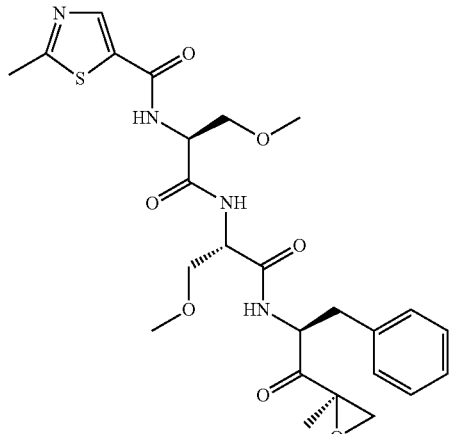

Oprozomib

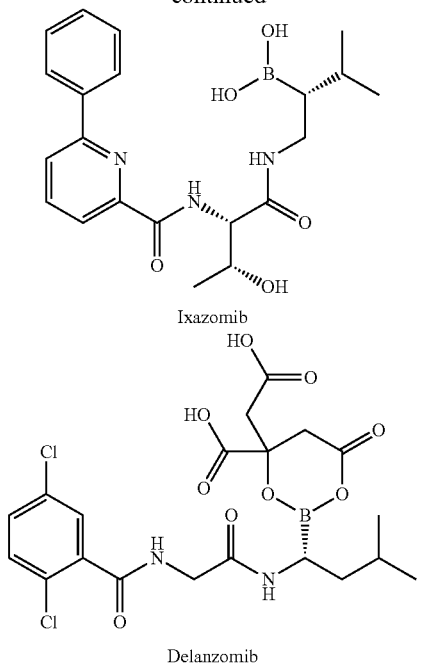

Ixazomib

Delanzomib

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, (e.g., diabetic retinopathy or other retinopathies), cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis and desmoid tumors. Non-cancerous proliferative disorders also include hyperproliferation of cells in the skin such as psoriasis and its varied clinical forms, Reiter's syndrome, pityriasis rubra pilaris, hyperproliferative variants of disorders of keratinization (e.g., actinic keratosis, senile keratosis), scleroderma, and the like. In one embodiment, the proliferative disorder is a myeloproliferative disorder. In one aspect, the myeloproliferative disorder is polycythemia vera, idiopathic myelofibrosis, myelodysplastic syndrome, psoriasis or essential thrombocythemia. In one embodiment, the proliferative disorder expresses JAK2V617F mutation of JAK2. In an aspect of this embodiment, the proliferative disorder is polycythemia vera, idiopathic myelofibrosis, or essential thrombocythemia. In one aspect, the proliferative disorder is polycythemia vera.

As used herein, the term "pharmaceutically acceptable salt" refers to a salt prepared from the compound of formula I, IA, or compound 1 and a pharmaceutically acceptable inorganic or organic acid. Suitable acids include such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, malic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Preferably, the acid is malic acid.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON, J. P., REMINGTON'S PHARMACEUTICAL SCIENCES (Mack Pub. Co., 17$^{th}$ ed., 1985). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate, and the like. Methods for encapsulating compositions, such as in a coating of hard gelatin or cyclodextran, are known in the art. See BAKER, ET AL., CONTROLLED RELEASE OF BIOLOGICAL ACTIVE AGENTS, (John Wiley and Sons, 1986).

As used herein, the term "effective amount" refers to an amount of a compound described herein which is sufficient to reduce or ameliorate the severity, duration, progression, or onset of a disease or disorder, delay onset of a disease or disorder, retard or halt the advancement of a disease or disorder, cause the regression of a disease or disorder, prevent or delay the recurrence, development, onset or progression of a symptom associated with a disease or disorder, or enhance or improve the therapeutic effect(s) of another therapy. In one embodiment of the invention, the disease or disorder is a proliferative disorder. The precise amount of compound administered to a subject will depend on the mode of administration, the type and severity of the disease or condition and on the characteristics of the subject, such as general health, age, sex, body weight and tolerance to drugs. For example, for a proliferative disease or disorder, determination of an effective amount will also depend on the degree, severity and type of cell proliferation. The skilled artisan will be able to determine appropriate dosages depending on these and other factors. When co-administered with other therapeutic agents, e.g., when co-administered with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound being used. In cases where no amount is expressly noted, an effective amount should be assumed. Non-limiting examples of an effective amount of a compound described herein are provided herein below. In a specific embodiment, the invention provides a method of treating, managing, or ameliorating a disease or disorder, e.g. a proliferative disorder, or one or more symptoms thereof, the method comprising administering to a subject in need thereof a dose of the compound of formula I, IA, or compound 1 up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

The dosage of an individual proteasome inhibitor used herein may be equal to or lower than the dose of an individual therapeutic agent when given independently to treat, manage, or ameliorate a disease or disorder, or one or more symptoms thereof. In one embodiment, the disease or disorder being treated with a combination therapy is a proliferative disorder. In another embodiment, the proliferative disorder is cancer. The recommended dosages of therapeutic agents currently used for the treatment, management, or amelioration of a disease or disorder, or one or more symptoms thereof, can obtained from any reference in the art. See, e.g., GOODMAN & GILMAN'S THE PHARMACOLOGICAL BASIS OF BASIS OF THERAPEUTICS $9^{TH}$ ED, (Hardman, et al., Eds., NY:Mc-Graw-Hill (1996)); PHYSICIAN'S DESK REFERENCE $57^{TH}$ ED. (Medical Economics Co., Inc., Montvale, N.J. (2003)).

As used herein, the terms "treat", "treatment" and "treating" refer to the reduction or amelioration of the progression, severity and/or duration of a disease or disorder, delay of the onset of a disease or disorder, or the amelioration of one or more symptoms (preferably, one or more discernible symptoms) of a disease or disorder, resulting from the administration of one or more therapies (e.g., one or more therapeutic agents such as a compound of the invention). The terms "treat", "treatment" and "treating" also encompass the reduction of the risk of developing a disease or disorder, and the delay or inhibition of the recurrence of a disease or disorder. In one embodiment, the disease or disorder being treated is a proliferative disorder such as cancer. In specific embodiments, the terms "treat", "treatment" and "treating" refer to the amelioration of at least one measurable physical parameter of a disease or disorder, such as growth of a tumor, not necessarily discernible by the patient. In other embodiments the terms "treat", "treatment" and "treating" refer to the inhibition of the progression of a disease or disorder, e.g., a proliferative disorder, either physically by the stabilization of a discernible symptom, physiologically by the stabilization of a physical parameter, or both. In another embodiment, the terms "treat", "treatment" and "treating" of a proliferative disease or disorder refers to the reduction or stabilization of tumor size or cancerous cell count, and/or delay of tumor formation. In another embodiment, the terms "treat", "treating" and "treatment" also encompass the administration of a compound described herein as a prophylactic measure to patients with a predisposition (genetic or environmental) to any disease or disorder described herein.

As used herein, the terms "therapeutic agent" and "therapeutic agents" refer to any agent(s) that can be used in the treatment of a disease or disorder, e.g. a proliferative disorder, or one or more symptoms thereof. In certain embodiments, the term "therapeutic agent" refers to a compound described herein. In certain other embodiments, the term "therapeutic agent" does not refer to a compound described herein. Preferably, a therapeutic agent is an agent that is known to be useful for, or has been or is currently being used for the treatment of a disease or disorder, e.g., a proliferative disorder, or one or more symptoms thereof.

As used herein, the term "synergistic" refers to a combination of a compound described herein and another therapeutic agent, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of the agent(s) to a subject with a disease or disorder, e.g., a proliferative disorder. The ability to utilize lower the dosage of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone.

As used herein, the phrase "side effects" encompasses unwanted and adverse effects of a therapeutic agent. Side effects are always unwanted, but unwanted effects are not necessarily adverse. An adverse effect from a therapeutic agent might be harmful or uncomfortable or risky to a subject. Side effects include fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapeutic agent. The use of the term "in combination" does not restrict the order in which the therapeutic agents are administered to a subject with a disease or disorder, e.g., a proliferative disorder. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as an anti-cancer agent, to a subject with a disease or disorder, e.g. a proliferative disorder, such as cancer. In one embodiment, the compound of formula I, IA, or compound 1, or a pharmaceutically acceptable salt thereof, and the proteasome inhibitor are dosed on independent schedules. In another embodiment, the compound of formula I, IA, or compound 1, or a pharmaceutically acceptable salt thereof, and the proteasome inhibitor are dosed on approximately the same schedule. In another embodiment, the compound of formula I, IA, or compound 1, or a pharmaceutically acceptable salt thereof, and the proteasome inhibitor are dosed concurrently or sequentially on the same day.

As used herein, the terms "therapies" and "therapy" can refer to any protocol(s), method(s), and/or agent(s) that can be used in the prevention, treatment, management, or amelioration of a disease or disorder, e.g., a proliferative disorder, or one or more symptoms thereof.

As used herein, a "protocol" includes dosing schedules and dosing regimens. The protocols herein are methods of use and include therapeutic protocols.

As used herein, a composition that "substantially" comprises a compound means that the composition contains more than about 80% by weight, more preferably more than about 90% by weight, even more preferably more than about 95% by weight, and most preferably more than about 97% by weight of the compound.

The compounds described herein are defined by their chemical structures and/or chemical names. Where a compound is referred to by both a chemical structure and a chemical name, and the chemical structure and the chemical name conflict, the chemical structure is determinative of the compound's identity.

When administered to a subject (e.g., a non-human animal for veterinary use or for improvement of livestock or to a human for clinical use), the compounds described herein are administered in an isolated form, or as the isolated form in a pharmaceutical composition. As used herein, "isolated" means that the compounds described herein are separated from other components of either: (a) a natural source, such as a plant or cell, preferably bacterial culture, or (b) a synthetic organic chemical reaction mixture. Preferably, the compounds described herein are purified via conventional techniques. As used herein, "purified" means that when isolated, the isolate contains at least 95%, preferably at least 98%, of a compound described herein by weight of the isolate either as a mixture of stereoisomers, or as a diastereomeric or enantiomeric pure isolate.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

The C-Met inhibitor in the combination is a compound of formula I:

Formula I or a pharmaceutically acceptable salt thereof or a pharmaceutical composition comprising the compound of formula I and a pharmaceutically acceptable carrier, wherein:
  $R^1$ is halo;
  $R^2$ is halo; and
  Q is CH or N.

In another embodiment, the C-Met inhibitor of formula I is a compound of formula IA:

Formula IA or a pharmaceutically acceptable salt thereof.

In another embodiment, the C-Met inhibitor of formula I is compound 1:

Formula IA or a pharmaceutically acceptable salt thereof.

In these and other embodiments, the compound of formula I, IA or compound 1, or a pharmaceutically acceptable salt thereof, is administered as a pharmaceutical composition, wherein the pharmaceutical composition additionally comprises a pharmaceutically acceptable carrier, excipient, or diluent. In a specific embodiment, the compound of formula I is compound 1.

The compound of formula I or compound 1, as described herein, includes both the recited compounds as well as individual isomers and mixtures of isomers. In each instance, the compound of formula I includes the pharmaceutically acceptable salts, hydrates, and/or solvates of the recited compounds and any individual isomers or mixture of isomers thereof.

In other embodiments, the compound of formula I or compound 1 can be the malate salt. The malate salt of the compound of formula I and of compound 1 is disclosed in PCT/US2010/021194 and U.S. Patent Application Ser. No. 61/325,095, the entire contents of each of which are incorporated herein by reference.

In other embodiments, the compound of formula I can be malate salt.

In other embodiments, the compound of formula I can be the (D)-malate salt.

In other embodiments, the compound of formula I can be the (L)-malate salt.

In other embodiments, the compound of formula IA can be malate salt.

In other embodiments, the compound of formula IA can be the (D)-malate salt.

In other embodiments, the compound of formula IA can be the (L)-malate salt.

In other embodiments, compound 1 can be the malate salt.

In other embodiments, compound 1 can be (D)-malate salt.

In other embodiments, compound 1 can be the (L)-malate salt.

In another embodiment, the malate salt of compound 1 is in the crystalline N-2 or N-1 form of the (L) malate salt and/or the (D) malate salt. In other embodiments, compound 1 is in a mixture of crystalline malate salt forms. The properties of crystalline enantiomers, including the N-1 and/or the N-2 crystalline forms of the malate salt of compound 1. Methods of making and characterizing such forms are fully described in PCT/US10/21194, which is incorporated herein by reference in its entirety.

In one embodiment the compound of formula I, IA, or compound 1 is administered concurrently (at the same time) or sequentially (one after the other) with the proteasome inhibitor. In a further embodiment, compound 1 and the proteasome inhibitor are administered once daily. In a further embodiment, compound 1 and the proteasome inhibitor are administered with fasting (i.e., without eating) for approximately two hours before and 1 hour after administration.

In another embodiment, compound 1 or a pharmaceutically acceptable salt thereof is administered orally once daily as a tablet or capsule as the free base or the malate salt.

The amount of the compound of formula I, IA, or compound 1 and the proteasome inhibitor that are administered will vary.

In these and other embodiments, compound 1 is administered orally once daily as its free base or as the malate salt as a capsule or tablet. In a further embodiment, compound 1 is administered as the L-malate salt. In a further embodiment:
- up to and including 100 mg of compound 1 is administered;
- up to and including 95 mg of compound 1 is administered;
- up to and including 90 mg of compound 1 is administered;
- up to and including 85 mg of compound 1 is administered;
- up to and including 80 mg of compound 1 is administered;
- up to and including 75 mg of compound 1 is administered;
- up to and including 70 mg of compound 1 is administered;
- up to and including 65 mg of compound 1 is administered;
- up to and including 60 mg of compound 1 is administered;
- up to and including 55 mg of compound 1 is administered;
- up to and including 50 mg of compound 1 is administered;
- up to and including 45 mg of compound 1 is administered;
- up to and including 40 mg of compound 1 is administered;
- up to and including 35 mg of compound 1 is administered;
- up to and including 30 mg of compound 1 is administered;
- up to and including 25 mg of compound 1 is administered;
- up to and including 20 mg of compound 1 is administered;
- up to and including 15 mg of compound 1 is administered;
- up to and including 10 mg of compound 1 is administered; or
- up to and including 5 mg of compound 1 is administered.

In another embodiment, compound 1 is administered as the malate salt orally once daily as a tablet as provided in the following table.

| Ingredient | (% w/w) |
| --- | --- |
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

In another embodiment, compound 1 is administered orally as the malate salt once daily as a tablet as provided in the following table.

| Ingredient | (% w/w) |
| --- | --- |
| Compound 1 | 25.0-33.3 |
| Microcrystalline Cellulose | q.s |
| Hydroxypropyl Cellulose | 3 |
| Poloxamer | 0-3 |
| Croscarmellose Sodium | 6.0 |
| Colloidal Silicon Dioxide | 0.5 |
| Magnesium Stearate | 0.5-1.0 |
| Total | 100 |

In another embodiment, compound 1 is administered orally as the malate salt once daily as a tablet as provided in the following table.

| Ingredient | Theoretical Quantity (mg/unit dose) |
| --- | --- |
| Compound 1 | 100.0 |
| Microcrystalline Cellulose PH-102 | 155.4 |
| Lactose Anhydrous 60M | 77.7 |
| Hydroxypropyl Cellulose, EXF | 12.0 |
| Croscarmellose Sodium | 24 |
| Colloidal Silicon Dioxide | 1.2 |
| Magnesium Stearate (Non-Bovine) | 3.0 |
| Opadry Yellow | 16.0 |
| Total | 416 |

In another embodiment, compound 1 is administered orally as the malate salt once daily as a tablet as provided in the following table.

| Ingredient | Function | % w/w |
| --- | --- | --- |
| Cabozantinib Drug Substance (25% drug load as free base) | Active Ingredient | 31.7 |
| Microcrystalline Cellulose (Avicel PH-102) | Filler | 38.9 |
| Lactose Anhydrous (60M) | Filler | 19.4 |
| Hydroxypropyl Cellulose (EXF) | Binder | 3.0 |
| Croscarmellose Sodium (Ac-Di-Sol) | Disenegrant | 6.0 |
| Colloidal Silicon Dioxide, | Glidant | 0.3 |
| Magnesium Stearate | Lubricant | 0.75 |
| Opadry Yellow Film Coating which includes: | | |
| HPMC 2910/Hypromellose 6 cp | Film Coating | 4.00 |
| Titanium dioxide | | |
| Triacetin | | |
| Iron Oxide Yellow | | |

In another embodiment, compound 1 is administered orally as the malate salt once daily as a capsule as provided in one of the following tables.

| Ingredient | % w/w |
| --- | --- |
| Compound 1 L-Malate Salt (10% drug load as free base) | 12.67 |
| MCC | 51.52 |
| Lactose | 25.76 |
| Hydroxypropyl cellulose | 3.0 |
| Croscarmellose Sodium | 6.0 |
| Colloidal Silicon Dioxide | 0.3 |
| Magnesium Stearate | 0.75 |
| Total | 100 |

| Ingredient | mg/unit dose |
| --- | --- |
| Compound 1 L-Malate Salt (10% drug load as free base) | 25 |
| Silicified Microcrystalline Cellulose | 196.75 |
| Croscarmellose sodium | 12.5 |
| Sodium starch glycolate | 12.5 |
| Fumed Silica | 0.75 |
| Stearic acid | 2.5 |
| Total Fill Weight | 250 |

| Ingredient | mg/unit dose |
| --- | --- |
| Compound 1 L-Malate Salt (50% drug load as free base) | 100 |
| Silicified Microcrystalline Cellulose | 75.40 |
| Croscarmellose sodium | 10.00 |
| Sodium Starch Glycolate | 10.00 |
| Fumed silica | 0.6 |
| Stearic Acid | 4.0 |
| Total Fill Weight | 200 |

| Ingredient | mg/unit dose 50 mg |
| --- | --- |
| Compound 1 L-Malate Salt (10% drug load as free base) | 63.35 |
| Microcrystalline Cellulose | 95.39 |
| Croscarmellose sodium | 9.05 |
| Sodium starch glycolate | 9.05 |
| Fumed Silica | 0.54 |
| Stearic acid | 3.62 |
| Total Fill Weight | 181.00 |

| Ingredient | mg/unit dose 60 mg |
| --- | --- |
| Compound 1 L-Malate Salt | 73.95 |
| Microcrystalline Cellulose | 114.36 |
| Croscarmellose sodium | 10.85 |
| Sodium starch glycolate | 10.85 |
| Fumed Silica | 0.65 |
| Stearic acid | 4.34 |
| Total Fill Weight | 217.00 |

Any of the formulations provided above can be adjusted according to the dose of compound 1 desired. Thus, the amount of each of the formulation ingredients can be proportionally adjusted to provide a tablet formulation containing various amounts of compound 1 as provided in the previous paragraphs. In another embodiment, the formulations can contain 20, 40, 60, or 80 mg of compound 1.

In one embodiment, the combination includes a pharmaceutical composition or a single unit dosage form containing both a compound of formula I or IA or compound 1, or a pharmaceutically acceptable salt thereof and a proteasome inhibitor. Pharmaceutical combinations and dosage forms described herein comprise the two active ingredients in relative amounts and formulated in such a way that a given pharmaceutical combination or dosage form can be used to treat proliferative disorders, such as cancer. In other embodiments, the compound of formula I or IA or compound 1 and the proteasome inhibitor may be in individual or separate pharmaceutical compositions, depending on the dosing schedules, preferred routes of administration, and available formulations of the two inhibitors. Optionally, these embodiments can also contain one or more additional therapeutic agents.

The pharmaceutical combinations described herein are formulated to be compatible with its intended route of administration. Examples of routes of administration include parenteral, e.g., intravenous, intradermal, subcutaneous, oral, intranasal (e.g., inhalation), transdermal (topical), transmucosal, and rectal administration. In a specific embodiment, the combination is formulated in accordance with routine procedures as a pharmaceutical composition adapted for intravenous, subcutaneous, intramuscular, oral, intranasal or topical administration to human beings. In one embodiment, the combination is formulated in accordance with routine procedures for subcutaneous administration to human beings.

In a specific embodiment, the combination therapies described herein comprise one or more compounds and at least one other therapy which has the same mechanism of action as the compounds. In another specific embodiment, the combination therapies described herein comprise one or more compounds described herein and at least one other therapy which has a different mechanism of action than the compounds. In certain embodiments, the combination therapies described herein improve the therapeutic effect of the compound of formula I or IA or compound 1, or a pharmaceutically acceptable salt thereof described herein by functioning together with the proteasome inhibitor to have an additive or synergistic effect. In certain embodiments, the combination therapies described herein reduce the side effects associated with the therapies. In certain embodiments, the combination therapies described herein reduce the effective dosage of one or more of the therapies.

In a specific embodiment, the combination comprising compound of formula I or IA or compound 1, or a pharmaceutically acceptable salt thereof is administered to a subject, preferably a human, to prevent, treat, manage, or ameliorate cancer, or one or more symptom thereof. In accordance with the invention, the pharmaceutical combinations described herein may also comprise one or more other agents being used, have been used, or are known to be useful in the treatment or amelioration of cancer, particularly colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, gastrointestinal stromal tumor (GIST), solid tumor, hematological tumor, or multiple myeloma. The pharmaceutical combinations described herein utilize pharmaceutical compositions and dosage forms which comprise one or more excipients. Suitable excipients are well known to those skilled in the art of pharmacy.

The present invention also provides a method of treating a proliferative disorder in a subject, comprising administering to the subject an effective amount of the combination of compound of formula I, IA, or compound 1, or a pharmaceutically acceptable salt thereof, and a proteasome inhibitor as described herein. In one embodiment, the proliferative disorder is cancer. In one aspect of this embodiment, the cancer is colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, gastrointestinal stromal tumor (GIST), or multiple myeloma. In another aspect of this embodiment, the cancer is non-small cell lung cancer, colon cancer, head and neck cancer, solid tumor, hematological tumor, or multiple myeloma.

Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

In one embodiment, the disclosed method is believed to be effective in treating a subject with non-solid tumors such as multiple myeloma. In another embodiment, the disclosed method is believed to be effective against T-cell leukemia, e.g., as exemplified by Jurkat and CEM cell lines; B-cell leukemia, e.g., as exemplified by the SB cell line; promyelocytes, e.g., as exemplified by the HL-60 cell line; uterine sarcoma, e.g., as exemplified by the MES-SA cell line; monocytic leukemia, e.g., as exemplified by the THP-1 (acute) cell line; and lymphoma, e.g., as exemplified by the U937 cell line.

Some of the disclosed methods can be also effective at treating subjects whose cancer has become "drug resistant" or "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. "Drug resistant" tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Other anti-proliferative or anti-cancer therapies may be combined with the compounds described herein to treat proliferative diseases and cancer. Other therapies or anti-cancer agents that may be used in combination with the anti-cancer agents described herein include surgery, radiotherapy (including gamma-radiation, neutron beam radiotherapy, electron beam radiotherapy, proton therapy, brachytherapy, and systemic radioactive isotopes), endocrine therapy, biologic response modifiers (including interferons, interleukins, and tumor necrosis factor (TNF)), hyperthermia and cryotherapy, agents to attenuate any adverse effects (e.g., antiemetics), and other approved chemotherapeutic drugs.

The therapeutic agents of the combination therapies described herein can be administered sequentially or concurrently. In one embodiment, the administration of the compound of formula I or IA or compound 1, or a pharmaceutically acceptable salt thereof and the proteasome inhibitor are done concurrently. In another embodiment, the administration of compound of formula I or IA or compound 1, or a pharmaceutically acceptable salt thereof and the proteasome inhibitor are done separately. In another embodiment, the administration of compound of formula I or IA or compound 1 and the proteasome inhibitor are done sequentially. In one embodiment, the administration of compound of formula I or IA or compound 1, or a pharmaceutically acceptable salt thereof and the proteasome inhibitor are done until the cancer is cured or stabilized or improved.

In one specific embodiment, the present method includes treating, managing, or ameliorating cancer, or one or more symptoms thereof, comprising administering to a subject in need thereof the compound of formula I or IA or compound 1, or a pharmaceutically acceptable salt thereof, in combination with a proteasome inhibitor such as epigallocatechin-3-gallate, salinosporamide A, carfilzomib, bortezomib, oprozomib, ixazomib, marizomib, or delanzomib, wherein the cancer is selected from the group consisting of colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, gastrointestinal stromal tumor (GIST), solid tumor, hematological tumor, or multiple myeloma.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is selected from the group consisting of epigallocatechin-3-gallate, salinosporamide A, carfilzomib, bortezomib, oprozomib, ixazomib, marizomib, or delanzomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is epigallocatechin-3-gallate. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is salinosporamide A. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is selected from the group consisting of carfilzomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is bortezomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is oprozomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is ixazomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is marizomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In another embodiment, the method of treating a subject with cancer includes administering to the subject an effective amount of the compound of formula I or IA or compound 1, or a pharmaceutically acceptable salt thereof, in combination with an effective amount of a proteasome inhibitor, wherein the proteasome inhibitor is delanzomib. In one embodiment, the cancer is breast cancer, colorectal cancer, colon cancer, non-small cell lung cancer, head and neck cancer, solid cancer, hematological cancer, or multiple myeloma. In one embodiment, the amount of the compound of formula I or IA or compound 1, is administered is from about 100 mg to about 5 mg. In one embodiment, the amount of compound of formula I or IA or compound 1, or a pharmaceutically acceptable salt thereof administered is from about up to and including 100 mg of compound 1 is administered; up to and including 95 mg of compound 1 is administered; up to and including 90 mg of compound 1 is administered; up to and including 85 mg of compound 1 is administered; up to and including 80 mg of compound 1 is administered; up to and including 75 mg of compound 1 is administered; up to and including 70 mg of compound 1 is administered; up to and including 65 mg of compound 1 is administered; up to and including 60 mg of compound 1 is administered; up to and including 55 mg of compound 1 is administered; up to and including 50 mg of compound 1 is administered; up to and including 45 mg of compound 1 is administered; up to and including 40 mg of compound 1 is administered; up to and including 35 mg of compound 1 is administered; up to and including 30 mg of compound 1 is administered; up to and including 25 mg of compound 1 is administered; up to and including 20 mg of compound 1 is administered; up to and including 15 mg of compound 1 is administered; up to and including 10 mg of compound 1 is administered; or up to and including 5 mg of compound 1 is administered. In one embodiment, compound 1 is administered once daily. In another embodiment, compound 1 is administered twice daily.

In yet another embodiment, the method of treating a subject with cancer, wherein the subject is being or has been treated with a chemotherapeutic agent, includes administering to the subject an effective amount of compound of formula I or IA or compound 1, or a pharmaceutically acceptable salt thereof, in combination with a proteasome inhibitor selected from the group consisting of epigallocatechin-3-gallate, salinosporamide A, carfilzomib, bortezomib, oprozomib, ixazomib, marizomib, or delanzomib.

In one embodiment, the method of treating a subject with cancer, wherein the subject is being or has been treated with a chemotherapeutic agent, includes administering to the subject an effective amount of the compound of formula I or IA or compound 1, or a pharmaceutically acceptable salt thereof, in combination with a proteasome inhibitor selected from the group consisting of epigallocatechin-3-gallate, salinosporamide A, carfilzomib, bortezomib, oprozomib, ixazomib, marizomib, or delanzomib, wherein the cancer is selected from the group consisting of colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, gastrointestinal stromal tumor (GIST), solid tumor, hematological tumor or multiple myeloma.

In one embodiment, the method of treating a subject with cancer includes a method wherein the subject has proven refractory to other therapies but is no longer on these therapies, includes administering to the subject an effective amount of the compound of formula I or IA or compound 1, or a pharmaceutically acceptable salt thereof, in combination with a proteasome inhibitor selected from the group consisting of epigallocatechin-3-gallate, salinosporamide A, carfilzomib, bortezomib, oprozomib, ixazomib, marizomib, or delanzomib, wherein the cancer is selected from the group consisting of colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, gastrointestinal stromal tumor (GIST), solid tumor, hematological tumor or multiple myeloma.

In another embodiment, the method also includes treating a subject with multiple myeloma, comprising administering to the subject an effective amount of a proteasome inhibitor and an effective amount of the compound of formula I or IA or compound 1, or a pharmaceutically acceptable salt thereof. In one embodiment, the proteasome inhibitor is bortezomib. In one embodiment, the proteasome inhibitor is carfilzomib.

In one embodiment, the method includes treating a subject with relapsed or refractory multiple myeloma, comprising administering to the subject an effective amount of a proteasome inhibitor and an effective amount of the compound of formula I or IA or compound 1, or a pharmaceutically acceptable salt thereof. In one embodiment, the proteasome inhibitor is bortezomib. In one embodiment, the proteasome inhibitor is carfilzomib.

In one further embodiment, the method includes inhibiting the growth of a cancer or tumor cell comprising the steps of: (a) contacting the cell with an effective amount of compound of formula I or IA or compound 1, or a pharmaceutically acceptable salt thereof; and (b) exposing the cell to an effective amount of a proteasome inhibitor selected from the group consisting of epigallocatechin-3-gallate, salinosporamide A, carfilzomib, bortezomib, oprozomib, ixazomib, marizomib, or delanzomib. In one embodiment, the proteasome inhibitor is bortezomib. In another embodiment, the proteasome inhibitor is carfilzomib.

Different therapeutically effective amounts may be applicable for different cancers, as will be readily known by those of ordinary skill in the art Similarly, amounts sufficient to prevent, manage, treat or ameliorate such cancers, but insufficient to cause, or sufficient to reduce, adverse effects associated with the compound of formula I or IA or compound 1, or a pharmaceutically acceptable salt thereof; are also encompassed by the above described dosage amounts and dose frequency schedules. Further, when a patient is administered multiple dosages of the compound of formula I, IA, or compound 1 described herein, not all of the dosages need be the same. For example, the dosage administered to the patient may be increased to improve the prophylactic or therapeutic effect of the compound or it may be decreased to reduce one or more side effects that a particular patient is experiencing.

In certain embodiments, when the compound of formula I or IA or compound 1, or a pharmaceutically acceptable salt thereof is administered in combination with a proteasome inhibitor, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies are administered within the same patient visit.

In certain embodiments, one or more compounds described herein and one or more other the therapies (e.g., therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound described herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10

EMBODIMENTS

The invention is further defined by the following non-limiting embodiments.

Embodiment 1

A pharmaceutical combination comprising a proteasome inhibitor and an inhibitor of C-Met according to the formula:

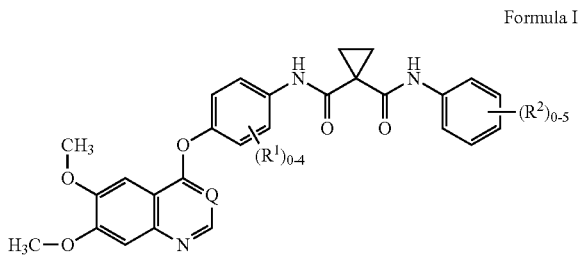

Formula I or a pharmaceutically acceptable salt thereof or a pharmaceutical composition comprising the compound of formula I and a pharmaceutically acceptable carrier, wherein:

$R^1$ is halo;
$R^2$ is halo; and
Q is CH or N.

Embodiment 2

The combination of claim 1, wherein the C-Met inhibitor of formula I is a compound of formula IA:

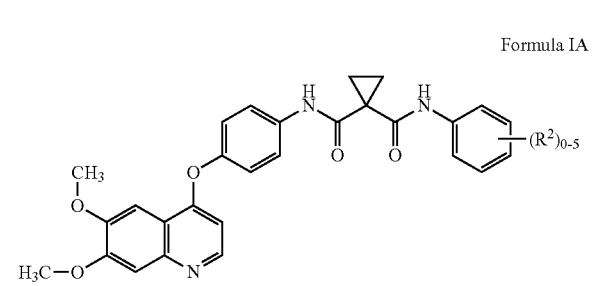

Formula IA or a pharmaceutically acceptable salt thereof.

Embodiment 3

The combination of claim 2, wherein the C-Met inhibitor of formula I is compound 1:

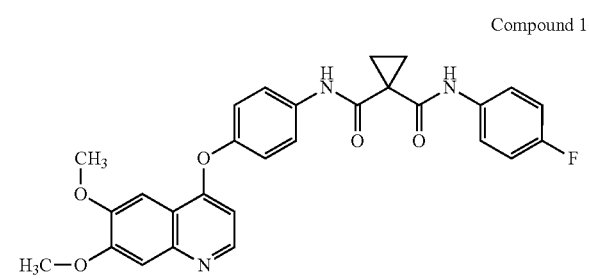 [SMILES: COc1cc2nccc(Oc3ccc(NC(=O)C4(C(=O)Nc5ccc(F)cc5)CC4)cc3)c2cc1OC]

Compound 1 or a pharmaceutically acceptable salt thereof.

Embodiment 4

The combination of claims 1-3, wherein compound 1 is the pharmaceutically acceptable L-malate salt, D-malate salt, DL malate salt, or a mixture thereof.

Embodiment 5

The combination of claims 1-3, wherein the proteasome inhibitor is epigallocatechin-3-gallate, salinosporamide A, carfilzomib, bortezomib, oprozomib, ixazomib, marizomib, or delanzomib.

Embodiment 6

The combination of claims 1-3, wherein the C-Met inhibitor is compound 1 or a pharmaceutically acceptable salt thereof, and the proteasome inhibitor is bortezomib.

Embodiment 7

The combination of claims 1-3, wherein the C-Met inhibitor is compound 1 or a pharmaceutically acceptable salt thereof, and the proteasome inhibitor is carfilzomib.

Embodiment 8

A method of treating a proliferative disorder in a subject, comprising administering to a subject an effective amount of the composition of claims 1-3.

Embodiment 9

The method of claim 10, wherein the proliferative disorder is cancer.

Embodiment 10

The method of claim 11, wherein the cancer is colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, multiple myeloma, solid tumor, hematological tumor, or gastrointestinal stromal tumor (GIST).

Embodiment 11

The method of claim 10, wherein the cancer is non-small cell lung cancer, colon cancer, multiple myeloma, or head and neck cancer.

Embodiment 12

The method of claim 11, wherein the cancer is multiple myeloma.

Embodiment 13

The method of claim 12, wherein the multiple myeloma is relapsed or refractory.

Embodiment 14

The method of any one of claims 10-13, wherein the subject is human.

Embodiment 15

A method for treating a subject with cancer, comprising administering to the subject an effective amount of a proteasome inhibitor and an effective amount of compound 1 or a pharmaceutically acceptable salt thereof, wherein the cancer is colorectal cancer, colon cancer, head and neck cancer, breast cancer, non-small cell lung cancer, prostate cancer, renal cell carcinoma, pancreatic cancer, ovarian cancer, peritoneal cancer, rectal cancer, kidney cancer, Hodgkin's lymphoma, bladder cancer, hepatocellular cancer, gastric cancer, squamous cell carcinoma, cervical cancer, uterine cancer, chronic lymphocytic leukemia, lymphoma, myeloma, multiple myeloma, solid tumor, hematological tumor, or gastrointestinal stromal tumor (GIST).

Embodiment 16

The method of claim 15, wherein the proteasome inhibitor is bortezomib or carfilzomib.

Embodiment 17

A method of inhibiting the growth of a cancer or tumor cell in a subject, the method comprising the steps of: (a) contacting the cell with an effective amount of a compound of formula I, IA, or compound 1 as defined in claims 1 and 3; and (b) exposing the cell to an effective amount of a proteasome inhibitor, wherein the proteasome inhibitor is selected from the group consisting of epigallocatechin-3-gallate, salinosporamide A, carfilzomib, bortezomib, oprozomib, ixazomib, marizomib, or delanzomib.

Embodiment 18

The method of claim 17, wherein the compound is compound 1 or a pharmaceutically acceptable salt thereof and the proteasome inhibitor is bortezomib or carfilzomib.

Preparation of Compound 1

Preparation of
1-(4-Fluorophenylcarbamoyl)cyclopropanecarboxylic acid (Compound A-1)

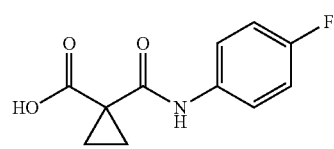 [SMILES: O=C(O)C1(C(=O)Nc2ccc(F)cc2)CC1]

The starting 1,1-cyclopropanedicarboxylic acid was treated with thionyl chloride (1.05 equivalents) in approximately 8 volumes of isopropyl acetate at 25° C. for 5 hours. The resulting mixture was then treated with a solution of 4-fluoroaniline (1.1 equivalents) and triethylamine (1.1 equivalents) in isopropyl acetate (2 volumes) over 1 hour. The product slurry was quenched with 5N NaOH solution (5 volumes), and the aqueous phase was discarded. The organic phase was extracted with 0.5N NaOH solution (10 volumes), and the basic extract was washed with heptane (5 volumes) and subsequently acidified with 30% HCl solution to give a slurry. compound A-1 was isolated by filtration.

Compound A-1 was prepared on a 1.00 kg scale using 1,1-cyclopropanedicarboxylic acid as the limiting reagent to furnish 1.32 kg of compound A-1 (77% isolated yield; 84% mass balance) with 99.92% purity (HPLC) and 100.3% assay.

Preparation of N-(4-{[6,7-bis(methyloxy)quinolin-4-yl]oxy}phenyl)-N'-(4-fluorophenyl)cyclopropane-1, 1-dicarboxamide (compound 1) and the (L)-malate salt Thereof A synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 1.

Scheme 1
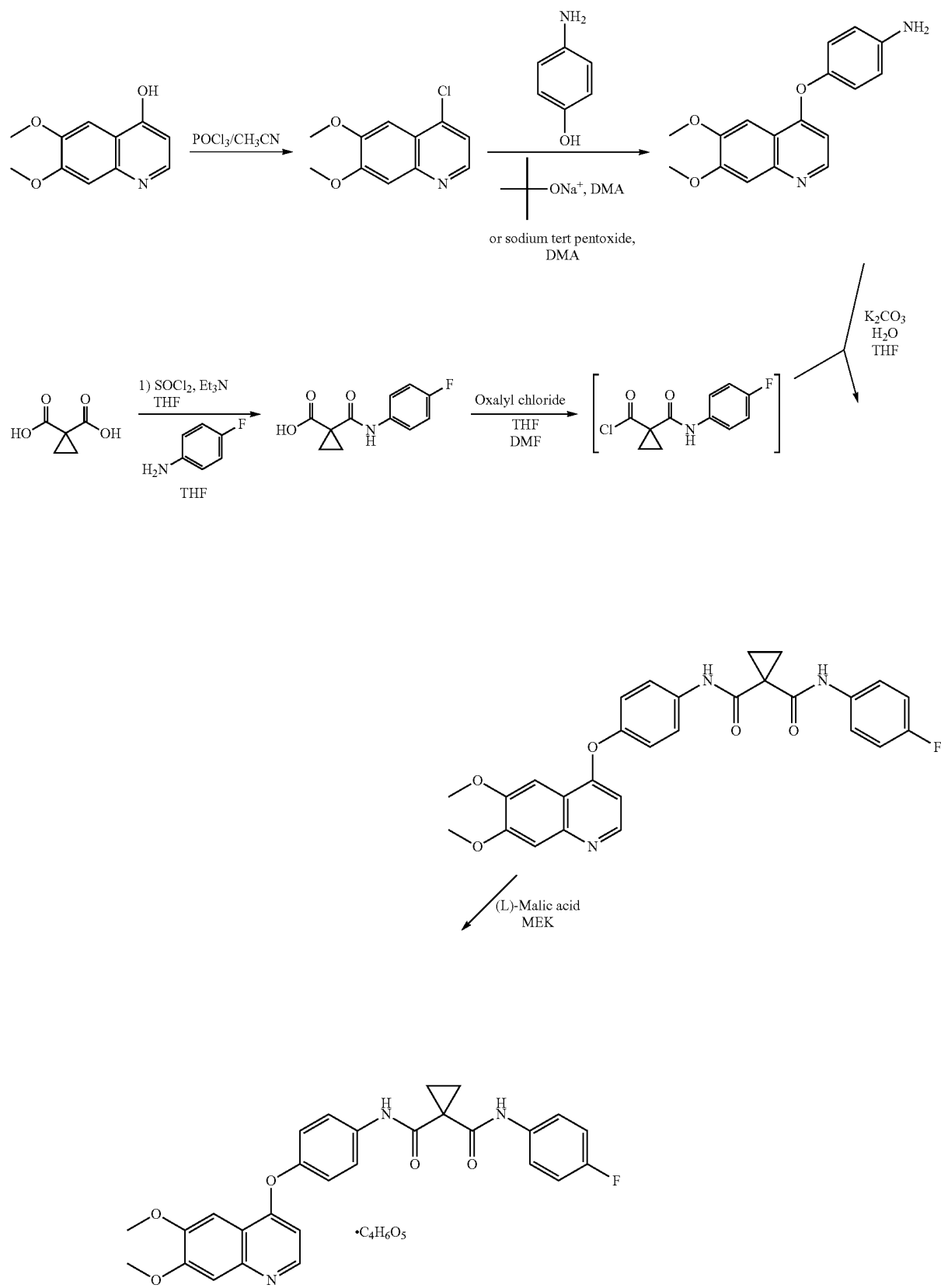

Another synthetic route that can be used for the preparation of N-(4-{[6,7-bis(methyloxy)quinolin-4-yl]oxy}phenyl)-N'-(4-fluorophenyl)cyclopropane-1,1-dicarboxamide and the (L)-malate salt thereof is depicted in Scheme 2.

was deemed complete (approximately 13 hours) when less than 3% of the starting material remained, as measured by in-process high-performance liquid chromatography [HPLC] analysis. The reaction mixture was cooled to approximately 2 to 7° C. and then quenched into a chilled

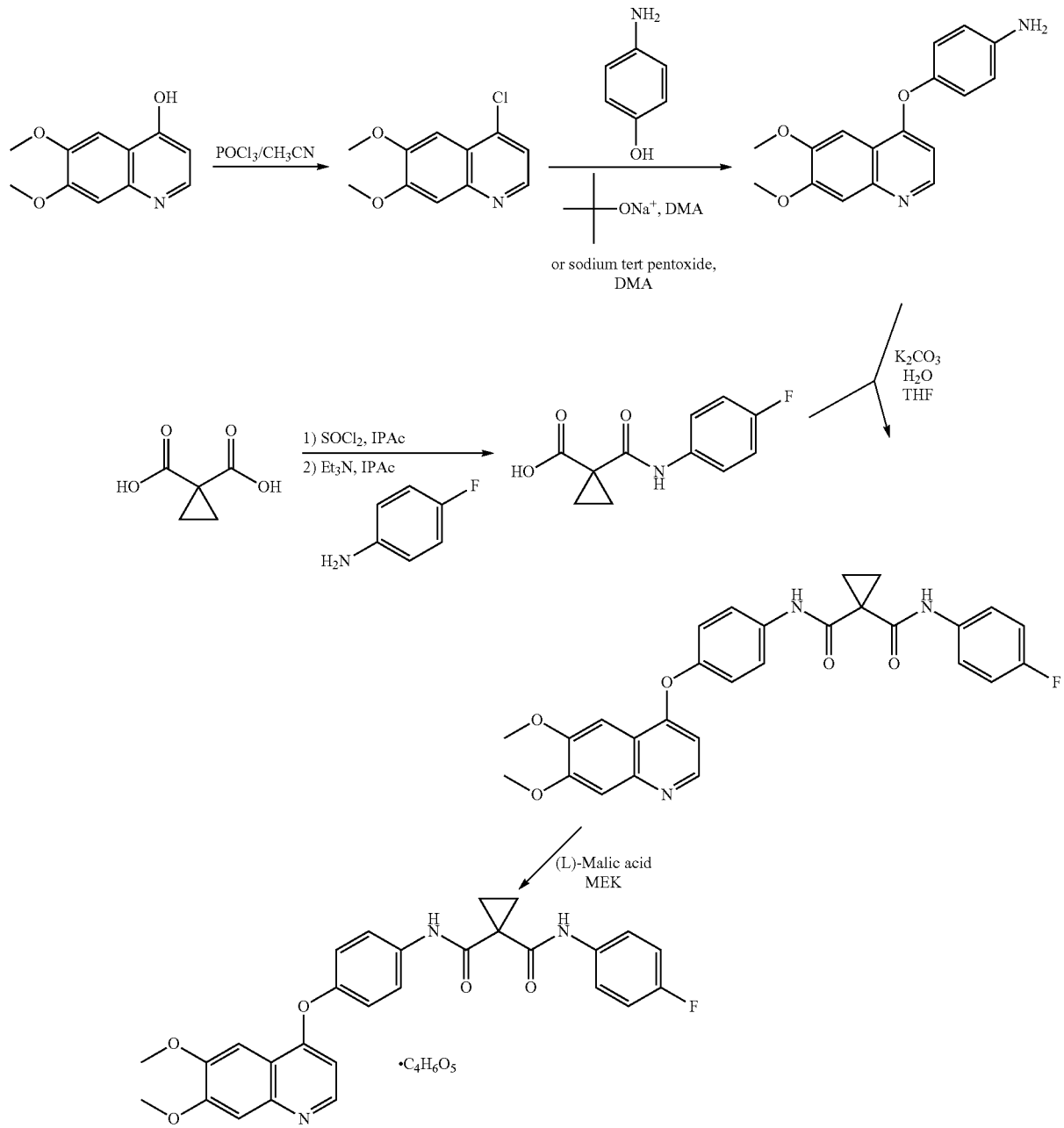

Preparation of 4-Chloro-6,7-dimethoxy-quinoline

A reactor was charged sequentially with 6,7-dimethoxy-quinoline-4-ol (47.0 kg) and acetonitrile (318.8 kg). The resulting mixture was heated to approximately 60° C., and phosphorus oxychloride (POCl₃, 130.6 kg) was added. After the addition of POCl₃, the temperature of the reaction mixture was raised to approximately 77° C. The reaction solution of dichloromethane (DCM, 482.8 kg), 26% NH₄OH (251.3 kg), and water (900 L). The resulting mixture was warmed to approximately 20 to 25° C., and phases were separated. The organic phase was filtered through a bed of AW hyflo super-cel NF (Celite; 5.4 kg), and the filter bed was washed with DCM (118.9 kg). The combined organic phase was washed with brine (282.9 kg) and mixed with water (120 L). The phases were separated, and the organic phase was concentrated by vacuum distillation with the removal of solvent (approximately 95 L residual volume). DCM (686.5 kg) was charged to the reactor containing organic phase and concentrated by vacuum distillation with the removal of solvent (approximately 90 L residual volume). Methyl t-butyl ether (MTBE, 226.0 kg) was then charged, and the temperature of the mixture was adjusted to −20 to −25° C. and held for 2.5 hours resulting in solid precipitate, which was then filtered, washed with n-heptane (92.0 kg), and dried on a filter at approximately 25° C. under nitrogen to afford the title compound (35.6 kg).

Preparation of 4-(6, 7-Dimethoxy-quinoline-4-yloxy)-phenylamine

4-Aminophenol (24.4 kg) dissolved in N,N-dimethylacetamide (DMA, 184.3 kg) was charged to a reactor containing 4-chloro-6,7-dimethoxyquinoline (35.3 kg), sodium t-butoxide (21.4 kg), and DMA (167.2 kg) at 20 to 25° C. This mixture was then heated to 100 to 105° C. for approximately 13 hours. After the reaction was deemed complete as determined using in-process HPLC analysis (less than 2% starting material remaining), the reactor contents were cooled at 15 to 20° C., and water (pre-cooled, 2 to 7° C., 587 L) was charged at a rate to maintain 15 to 30° C. temperature. The resulting solid precipitate was filtered, washed with a mixture of water (47 L) and DMA (89.1 kg), and finally washed with water (214 L). The filter cake was then dried at approximately 25° C. on filter to yield crude 4-(6, 7-dimethoxy-quinoline-4-yloxy)-phenylamine (59.4 kg wet, 41.6 kg dry calculated based on limit of detection, hereinafter "LOD"). Crude 4-(6, 7-dimethoxy-quinoline-4-yloxy)-phenylamine was refluxed (approximately 75° C.) in a mixture of tetrahydrofuran (THF, 211.4 kg) and DMA (108.8 kg) for approximately 1 hour, then cooled to 0 to 5° C., and aged for approximately 1 hour, after which time the solid was filtered, washed with THF (147.6 kg), and dried on a filter under vacuum at approximately 25° C. to yield 4-(6, 7-dimethoxy-quinoline-4-yloxy)-phenylamine (34.0 kg).

Alternative Preparation of 4-(6, 7-Dimethoxy-quinoline-4-yloxy)-phenylamine 4-chloro-6,7-dimethoxyquinoline (34.8 kg), 4-Aminophenol (30.8 kg), and sodium tert-pentoxide (1.8 equivalents) 88.7 kg, 35 weight percent in THF) were charged to a reactor, followed by N,N-dimethylacetamide (DMA, 293.3 kg). This mixture was then heated to 105 to 115° C. for approximately 9 hours. After the reaction was deemed complete as determined using in-process HPLC analysis (less than 2% starting material remaining), the reactor contents were cooled at 15 to 25° C., and water (315 kg) was added over a two hour period while maintaining the temperature between 20 and 30° C. The reaction mixture was then agitated for an additional hour at 20 to 25° C. The crude product was collected by filtration and washed with a mixture of 88 kg water and 82.1 kg DMA, followed by 175 kg water. The product was dried on a filter drier for 53 hours. The LOD showed less than 1% w/w.

In an alternative procedure, 1.6 equivalents of sodium tert-pentoxide were used, and the reaction temperature was increased from 110 to 120° C. In addition, the cool down temperature was increased to 35 to 40° C., and the starting temperature of the water addition was adjusted to 35 to 40° C., with an allowed exotherm to 45° C.

Preparation of 1-(4-Fluoro-phenylcarbamoyl)-cyclopropanecarbonyl chloride

Oxalyl chloride (12.6 kg) was added to a solution of 1-(4-fluoro-phenylcarbamoyl)-cyclopropanecarboxylic acid (22.8 kg) in a mixture of THF (96.1 kg) and N, N-dimethylformamide (DMF; 0.23 kg) at a rate such that the batch temperature did not exceed 25° C. This solution was used in the next step without further processing.

Alternative Preparation of 1-(4-Fluoro-phenylcarbamoyl)-cyclopropanecarbonyl chloride A reactor was charged with 1-(4-fluoro-phenylcarbamoyl)-cyclopropanecarboxylic acid (35 kg), DMF (344 g), and THF (175 kg). The reaction mixture was adjusted to 12 to 17° C., and then to the reaction mixture was charged 19.9 kg of oxalyl chloride over a period of 1 hour. The reaction mixture was left stirring at 12 to 17° C. for 3 to 8 hours. This solution was used in the next step without further processing.

Preparation of cyclopropane-1,1-dicarboxylic acid [4-(6,7-dimethoxy-quinoline-4-yloxy)-phenyl]-amide (4-fluoro-phenyl)-amide The solution from the previous step containing 1-(4-fluoro-phenylcarbamoyl)-cyclopropanecarbonyl chloride was added to a mixture of compound 4-(6,7-dimethoxy-quinoline-4-yloxy)-phenylamine (23.5 kg) and potassium carbonate (31.9 kg) in THF (245.7 kg) and water (116 L) at a rate such that the batch temperature did not exceed 30° C. When the reaction was complete (in approximately 20 minutes), water (653 L) was added. The mixture was stirred at 20 to 25° C. for approximately 10 hours, which resulted in the precipitation of the product. The product was recovered by filtration, washed with a pre-made solution of THF (68.6 kg) and water (256 L), and dried first on a filter under nitrogen at approximately 25° C. and then at approximately 45° C. under vacuum to afford the title compound (41.0 kg, 38.1 kg, calculated based on LOD).

Alternative Preparation of cyclopropane-1,1-dicarboxylic acid [4-(6,7-dimethoxy-quinoline-4-yloxy)-phenyl]-amide (4-fluoro-phenyl)-amide A reactor was charged with 4-(6,7-dimethoxy-quinoline-4-yloxy)-phenylamine (35.7 kg, 1 equivalent), followed by THF (412.9 kg). To the reaction mixture was charged a solution of $K_2CO_3$ (48.3 kg) in water (169 kg). The acid chloride solution of described in the Alternative Preparation of 1-(4-Fluoro-phenylcarbamoyl)-cyclopropanecarbonyl chloride above was transferred to the reactor containing 4-(6,7-dimethoxy-quinoline-4-yloxy)-phenylamine while maintaining the temperature between 20 to 30° C. over a minimum of two hours. The reaction mixture was stirred at 20 to 25° C. for a minimum of three hours. The reaction temperature was then adjusted to 30 to 25° C., and the mixture was agitated. The agitation was stopped, and the phases of the mixture were allowed to separate. The lower aqueous phase was removed and discarded. To the remaining upper organic phase was added water (804 kg). The reaction was left stirring at 15 to 25° C. for a minimum of 16 hours.

The product precipitated and was filtered and washed with a mixture of water (179 kg) and THF (157.9 kg) in two portions. The crude product was dried under a vacuum for at least two hours. The dried product was then taken up in THF (285.1 kg). The resulting suspension was transferred to reaction vessel and agitated until the suspension became a clear (dissolved) solution, which required heating to 30 to 35° C. for approximately 30 minutes. Water (456 kg) was then added to the solution, as well as SDAG-1 ethanol (20 kg, ethanol denatured with methanol over two hours). The mixture was agitated at 15 to 25° C. for at least 16 hours. The product was filtered and washed with a mixture of water (143 kg and 126.7 kg THF (143 kg) in two portions. The product was dried at a maximum temperature set point of 40° C.

In an alternative procedure, the reaction temperature during acid chloride formation was adjusted to 10 to 15° C. The recrystallization temperature was changed from 15 to 25° C. to 45 to 50° C. for 1 hour and then cooled to 15 to 25° C. over 2 hours.

Preparation of cyclopropane-1,1-dicarboxylic acid [4-(6,7-dimethoxy-quinoline-4-yloxy)-phenyl]-amide (4-fluoro-phenyl)-amide, cabozantinib (L) malate salt Cyclopropane-1,1-dicarboxylic acid [4-(6,7-dimethoxy-quinoline-4-yloxy)-phenyl]-amide (4-fluoro-phenyl)-amide (13.3 kg), L-malic acid (4.96 kg), methyl ethyl ketone (MEK; 188.6 kg) and water (37.3 kg) were charged to a reactor, and the mixture was heated to reflux (approximately 74° C.) for approximately 2 hours. The reactor temperature was reduced to 50 to 55° C., and the reactor contents were filtered. These sequential steps described above were repeated two more times starting with similar amounts of cyclopropane-1,1-dicarboxylic acid [4-(6,7-dimethoxy-quinoline-4-yloxy)-phenyl]-amide (4-fluoro-phenyl)-amide (13.3 kg), L-Malic acid (4.96 kg), MEK (198.6 kg), and water (37.2 kg). The combined filtrate was azeotropically dried at atmospheric pressure using MEK (1133.2 kg) (approximate residual volume 711 L; KF<0.5% w/w) at approximately 74° C. The temperature of the reactor contents was reduced to 20 to 25° C. and held for approximately 4 hours, resulting in solid precipitate which was filtered, washed with MEK (448 kg), and dried under vacuum at 50° C. to afford the title compound (45.5 kg).

Alternative Preparation of cyclopropane-1,1-dicarboxylic acid [4-(6,7-dimethoxy-quinoline-4-yloxy)-phenyl]-amide (4-fluoro-phenyl)-amide, (L) malate salt Cyclopropane-1,1-dicarboxylic acid [4-(6,7-dimethoxy-quinoline-4-yloxy)-phenyl]-amide (4-fluoro-phenyl)-amide (47.9 kg), L-malic acid (17.2 kg), methyl ethyl ketone (658.2 kg), and water (129.1 kg) were charged to a reactor, and the mixture was heated 50 to 55° C. for approximately 1 to 3 hours and then at 55 to 60° C. for an additional 4 to 5 hours. The mixture was clarified by filtration through a 1 µm cartridge. The reactor temperature was adjusted to 20 to 25° C. and vacuum distilled with a vacuum at 150 to 200 mm Hg with a maximum jacket temperature of 55° C. to the volume range of 558 to 731 L.

The vacuum distillation was performed two more times with the charge of 380 kg and 380.2 kg methyl ethyl ketone, respectively. After the third distillation, the volume of the batch was adjusted to 18 v/w of Cyclopropane-1,1-dicarboxylic acid [4-(6,7-dimethoxy-quinoline-4-yloxy)-phenyl]-amide (4-fluoro-phenyl)-amide by charging methyl ethyl ketone (159.9 kg) to give a total volume of 880 L. An additional vacuum distillation was carried out by adjusting methyl ethyl ketone (245.7 kg). The reaction mixture was left with moderate agitation at 20 to 25° C. for at least 24 hours. The product was filtered and washed with methyl ethyl ketone (415.1 kg) in three portions. The product was dried under a vacuum with the jacket temperature set point at 45° C.

In an alternative procedure, the order of addition was changed so that a solution of L-malic acid (17.7 kg) dissolved in water (129.9 kg) was added to Cyclopropane-1,1-dicarboxylic acid [4-(6,7-dimethoxy-quinoline-4-yloxy)-phenyl]-amide (4-fluoro-phenyl)-amide (48.7 kg) in methyl ethyl ketone (673.3 kg).

Effects of a Combination Treatment with Cabozantinib and Bortezomib in the 5TGM1 Murine Multiple Myeloma Model Cabozantinib is an inhibitor of tyrosine kinases including MET, VEGFR2, RET, and the TAM family kinases TYRO3, AXL, and MER. Cabozantinib has shown clinical activity in patients with castration-resistant prostate cancer and other solid tumors with bone metastases. Multiple myeloma (MM) is the second most common hematologic malignancy, and represents approximately 2% of all cancer deaths. MM is a monoclonal B-cell (plasma cell) neoplasia with clinical hallmarks of multiple osteolytic lesions causing bone pain, pathologic fractures, and hypercalcemia. Circulating levels of HGF and VEGF are upregulated in MM patients, and regulation of plasma cell-osteoblast communication by the HGF-MET signaling pathway has been implicated in the development of lytic bone disease in these patients. Thus, the primary objectives of this research were to A): determine the activity of cabo on bone lesions and tumor burden in the syngeneic 5TGM1 mouse MM model (study 1), and B): investigate the impact of cabozantinib on overall survival of these mice when dosed alone or in combination with bortezomib (study 2).

Test Compounds and Vehicles.

Cabozantinib (XL184) is obtained from the Exelixis in powder form. It is dissolved in sterile water to a concentration of 1 mg/ml for dosing at 10 mg/kg or 30 mg/kg. The dosing solution is prepared daily within one hour before dosing. The undissolved test compound will be stored at ambient or room temperature in a dry environment such as in a dessicator. The test compound is administered daily by oral gavage.

Bortezomib is obtained from LC Laboratories (Boston, Mass., USA) in powder form and dissolved in EtOH. The stock solution is stored at −20° C. The bortezomib dosing solutions are prepared fresh for every dosing as follows: 25 µl of the stock solution of 25 mg/ml of bortezomib (LC Laboratories, Boston, Mass., USA) in EtOH and 25 µl of EtOH is diluted in 3.61 ml of 0.9% NaCl to obtain the concentration of 0.17 mg/ml. The dosing volume is 3 ml/kg, resulting in the dose 0.5 mg/kg. Bortezomib is administered intraperitoneally twice a week.

The Cabozantinib vehicle (Vehicle 1) is sterile water and the bortezomib vehicle (Vehicle 2) is 0.7% EtOH in 0.9% NaCl.

Cell Culture.

5TGM1 mouse multiple myeloma cells are obtained from the Department of Molecular Medicine, University of Texas Health Science Center at San Antonio. Cell culturing is performed according to standard procedures. 5TGM1 mouse myeloma cells (2×106 cells in 0.1 ml of PBS) are inoculated into the tail vein of the mice at day 0. Viability of the cells will be determined before and after the inoculations. Cancer cell inoculation will cause the mice to develop a bone disease typical for multiple myeloma.

Blood Sampling.

Blood samples will be collected from the saphenous vein before the inoculation of cancer cells, at days 15, 22, 35 and at sacrifice. The serum samples will be prepared within one hour of sampling, and stored at −70° C. Serum paraprotein IgG2b will be analyzed using mouse IgG2b ELISA quantitation kit (Bethyl Laboratories Inc, Montgomery, Tex., USA). Serum TRACP 5b activity and PINP concentration will be analyzed using Mouse TRAP and Mouse PINP kits (IDS, Boldon, UK).

X-Ray Radiography.

The development of the myeloma bone disease is monitored by x-ray radiography at day 35. Animals will be anesthethized by isoflurane and x-rayed in a prone position with the Faxitron Specimen Radiographic System MX-20 D12 (Faxitron Corp. Illinois, USA) using Faxitron Dicom 3.0-software. At least one radiograph (both hind limbs) per animal will be taken on each x-ray occasion (31 kV, 10 seconds, magnification 2×). The lesion number and lesion area in hind limbs will be determined from the images with MetaMorph image analysis software.

Statistical Analysis.

Statistical analysis will be performed with statistical software R (version 2.14.0 or newer, www.r-project.org) or OriginPro (version 8.6 or newer, OriginLab, Northampton, Mass., USA). The mean and standard deviation of each parameter will be determined. All statistical analyses will be performed as two-sided tests. Normal distribution and homogeneity of variance will be checked before further analyses. In case of violating these assumptions, either log transformation or other appropriate transformation (e.g. square root, reciprocal) will be applied. If the assumptions are fulfilled as such or after transformation, Oneway ANOVA will be used for end-point parameters to assess whether the values obtained between groups are statistically different (with p<0.05) followed by Tukey test for comparison against the control group. If the assumptions are not fulfilled even after the transformations described above, rank-transformation will be applied and the non-parametric Kruskal-Wallis test followed by Mann-Whitney U-test will be used. Linear mixed effects model will be used for repeated measurements like biochemical markers.

Methods.

Female C57BL/KaLwRij mice were allocated to treatment groups (n=15 per group) with equivalent average body weights. Four experimental groups were utilized in each of 2 studies: a vehicle control group, and groups receiving single agent bortezomib (0.5 mg/kg ip twice a week) or cabozantinib (10 mg/kg, PO QD). Study 1 also included a higher dose cabozantinib group (30 mg/kg, PO QD), and study 2 included a combination group: bortezomib (0.5 mg/kg ip twice a week) plus cabozantinib (10 mg/kg, PO QD). In study 2, each single agent groups also received the vehicle from the alternate single-agent group via the appropriate route and schedule.

On day 0, animals were inoculated with 5TGM1 mouse myeloma cells by IV administration. Dosing began on day 1 and continued daily until euthanasia at day 35 (study 1) or day 70 (study 2). Body weights were determined twice a week and blood samples were collected on days—1, 15, 22, and 34 for analysis of paraprotein (IgG2b) and TRACP 5b.

In study 1 the development of osteolytic lesions was detected by radiography at the end of the study. Animals were euthanized before the end of the experiment for humane endpoints (i.e. paraplegia). Animals euthanized within four days of the end of the experiment in study 1 were included in the analyses.

Results.

In study 1, bortezomib reduced serum IgG2b levels, and decreased the frequency of soft tissue lesions, but did not show bone protective properties. Cabozantinb exhibited bone protective effects: mean and total area of osteolytic lesions were reduced at the 30 mg/kg dose, and serum TRACP 5b values and osteoclast counts at the tumor-bone interface were reduced at both the 10 and 30 mg/kg doses. Relative bone area did not differ from control according to histomorphometry. The rise in serum IgG2b started earlier than vehicle control in both cabozantinib-treated groups, but a significant difference was not observed in relative IgG2b at sacrifice. Cabozantinib dose dependently increased the necrotic tumor area in bone, indicating the possibility that the rise in IgG2b may have been due to lysis of plasma cells. Both doses of cabozantinib decreased the frequency of soft tissue lesions.

In study 2, the median survival times were 36 d (vehicle), 43 d (bortezomib), 48 d (cabozantinib), and 55 d (cabozantinib+bortezomib), as depicted in FIG. 1. The prolongation of overall survival (OS) compared to vehicle was statistically significant for the cabozantinib group but not for the bortezomib group. Prolongation of OS in the combination group was significant compared to bortezomib alone, but not when compared to cabozantinib alone.

Conclusions.

Cabozantinib showed both bone-protective and anti-tumor effects in this murine model of MM. In addition, statistically-significant prolongation of overall survival was observed with single agent cabozantinib and with the combination of cabozantinib+bortezomib. Based on these results, further investigation of cabozantinib alone or in combination with other agents in multiple myeloma is warranted.

The foregoing disclosure has been described in some detail by way of illustration and example for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The invention claimed is:

1. A method for treating a subject with multiple myeloma, comprising administering to the subject a combination therapy which comprises an effective amount of the proteasome inhibitor bortezomib and Compound 1:

Compound 1

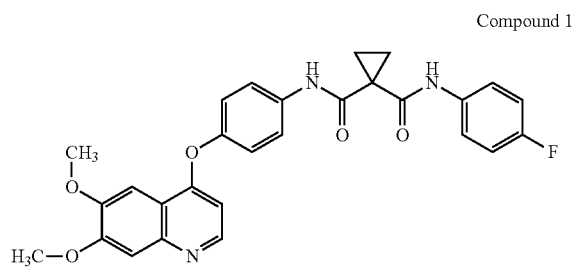 [SMILES: COc1cc2nccc(Oc3ccc(NC(=O)C4(C(=O)Nc5ccc(F)cc5)CC4)cc3)c2cc1OC]

as the L-malate salt, wherein Compound 1 as the L-malate salt is administered once daily as a pharmaceutical formulation as provided in one of the following tables

| Ingredient | (% w/w) |
|---|---|
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

| Ingredient | (% w/w) |
|---|---|
| Compound 1, L-malate salt | 31.68 |
| Microcrystalline Cellulose | 38.85 |
| Lactose anhydrous | 19.42 |
| Hydroxypropyl Cellulose | 3.00 |
| Croscarmellose Sodium | 6.00 |
| Silicon dioxide, Colloidal | 0.30 |
| Magnesium Stearate | 0.75 |
| Total | 100.00. |

2. A method of reducing mean and total area of osteolytic bone lesions in multiple myeloma human patients comprising administering to the patient an effective amount of the proteasome inhibitor bortezomib and Compound 1:

Compound 1 as the L-malate salt, wherein Compound 1 as the L-malate salt is administered once daily as a pharmaceutical formulation as provided in one of the following tables

| Ingredient | (% w/w) |
|---|---|
| Compound 1 | 31.68 |
| Microcrystalline Cellulose | 38.85 |
| Lactose anhydrous | 19.42 |
| Hydroxypropyl Cellulose | 3.00 |
| Croscarmellose Sodium | 3.00 |
| Total Intra-granular | 95.95 |
| Silicon dioxide, Colloidal | 0.30 |
| Croscarmellose Sodium | 3.00 |
| Magnesium Stearate | 0.75 |
| Total | 100.00 |

| Ingredient | (% w/w) |
|---|---|
| Compound 1, L-malate salt | 31.68 |
| Microcrystalline Cellulose | 38.85 |
| Lactose anhydrous | 19.42 |
| Hydroxypropyl Cellulose | 3.00 |
| Croscarmellose Sodium | 6.00 |
| Silicon dioxide, Colloidal | 0.30 |
| Magnesium Stearate | 0.75 |
| Total | 100.00. |

3. The method of claim 1, wherein the subject is human.

4. The method of claim 1, wherein the subject has bone lesions.

* * * * *